(12) United States Patent
Noh et al.

(10) Patent No.: US 10,238,303 B2
(45) Date of Patent: Mar. 26, 2019

(54) BLOOD PRESSURE MONITOR

(71) Applicant: Samsung Electronics Co., Ltd., Suwon-si (KR)

(72) Inventors: Seungwoo Noh, Seongnam-si (KR); Youn-ho Kim, Hwaseong-si (KR); Sangyun Park, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 305 days.

(21) Appl. No.: 14/993,378

(22) Filed: Jan. 12, 2016

(65) Prior Publication Data

US 2017/0055856 A1 Mar. 2, 2017

(30) Foreign Application Priority Data

Aug. 27, 2015 (KR) .................. 10-2015-0120722

(51) Int. Cl.
*A61B 5/022* (2006.01)
*A61B 5/0235* (2006.01)
*A61B 5/00* (2006.01)

(52) U.S. Cl.
CPC .......... *A61B 5/02233* (2013.01); *A61B 5/022* (2013.01); *A61B 5/0235* (2013.01); *A61B 5/6824* (2013.01); *A61B 2560/0209* (2013.01)

(58) Field of Classification Search
CPC ... A61B 5/02233; A61B 5/022; A61B 5/0235; A61B 5/6824; A61B 2560/0209
USPC .................. 600/490–499, 485; 137/331, 333, 137/565.25; 251/207, 230
See application file for complete search history.

(56) References Cited

U.S. PATENT DOCUMENTS

| | | | | |
|---|---|---|---|---|
| 4,370,983 | A | * | 2/1983 | Lichtenstein ............ A61B 5/00 600/301 |
| 4,464,172 | A | * | 8/1984 | Lichtenstein ............ A61B 5/00 604/65 |
| 5,062,775 | A | * | 11/1991 | Orth ........................ A61M 1/10 417/319 |
| 5,188,604 | A | * | 2/1993 | Orth ........................ A61M 1/10 128/DIG. 13 |
| 6,151,968 | A | | 11/2000 | Chou |
| 7,083,573 | B2 | | 8/2006 | Yamakoshi et al. |
| 7,094,216 | B2 | * | 8/2006 | Trombley, III ....... A61M 5/007 604/65 |

(Continued)

FOREIGN PATENT DOCUMENTS

JP 2008-237517 A 10/2008
JP 2013-158347 A 8/2013

(Continued)

*Primary Examiner* — Navin Natinithithadha
(74) *Attorney, Agent, or Firm* — NSIP Law

(57) ABSTRACT

A blood pressure monitor including a manually operable pressurizer is disclosed. The blood pressure monitor may include a cuff configured to apply a pressure to a target portion of a body of a user, a pressurizer, a depressurizer, and a sensor to measure a blood pressure. The pressurizer may include a rotator, and be configured to supply a fluid to the cuff, to cause the cuff to apply the pressure, through rotation of the rotator caused by an external rotational force applied to the blood pressure monitor to rotate the rotator. The depressurizer may be configured to reduce the applied pressure applied by the cuff to the target portion.

12 Claims, 13 Drawing Sheets

(56) References Cited

U.S. PATENT DOCUMENTS

| | | | |
|---|---|---|---|
| 7,326,186 B2* | 2/2008 | Trombley, III | A61M 5/007 604/131 |
| 7,338,434 B1* | 3/2008 | Haarstad | A61B 17/00234 600/201 |
| 8,075,493 B2* | 12/2011 | Kishimoto | A61B 5/02141 137/355.16 |
| 8,292,821 B2 | 10/2012 | Kato | |
| 8,500,692 B2* | 8/2013 | Yodfat | A61B 5/4839 604/131 |
| 8,652,058 B2 | 2/2014 | Kim et al. | |
| 8,747,358 B2* | 6/2014 | Trombley, III | A61M 5/007 604/151 |
| 9,572,924 B2* | 2/2017 | Yodfat | A61B 5/4839 |
| 9,585,574 B2* | 3/2017 | Nelson | A61B 5/02141 |
| 2007/0197923 A1* | 8/2007 | Kishimoto | A61B 5/02141 600/490 |
| 2009/0137914 A1 | 5/2009 | Young | |
| 2009/0322513 A1 | 12/2009 | Hwang et al. | |
| 2010/0106029 A1* | 4/2010 | Fraden | A61B 5/02208 600/493 |
| 2010/0331667 A1* | 12/2010 | Nelson | A61B 5/02141 600/411 |
| 2011/0004160 A1* | 1/2011 | Yodfat | A61B 5/4839 604/152 |
| 2011/0092828 A1* | 4/2011 | Spohn | A61M 5/007 600/485 |
| 2011/0282223 A1* | 11/2011 | Sano | A61B 5/02141 600/499 |
| 2011/0295130 A1* | 12/2011 | Tokko | A61B 5/02141 600/494 |
| 2012/0203119 A1* | 8/2012 | Yamashita | A61B 5/02225 600/490 |
| 2012/0215119 A1* | 8/2012 | Kawano | A61B 5/02141 600/490 |
| 2012/0232412 A1* | 9/2012 | Kinoshita | A61B 5/02225 600/498 |
| 2013/0023777 A1* | 1/2013 | Tokko | A61B 5/02116 600/494 |

FOREIGN PATENT DOCUMENTS

| | | |
|---|---|---|
| KR | 10-1473895 | 12/2014 |
| WO | WO 2013/169014 A1 | 11/2013 |

* cited by examiner

BLOOD PRESSURE MONITOR

CROSS-REFERENCE TO RELATED APPLICATION(S)

This application claims the benefit under 35 USC 119(a) of Korean Patent Application No. 10-2015-0120722, filed on Aug. 27, 2015 in the Korean Intellectual Property Office, the entire disclosure of which is incorporated herein by reference for all purposes.

BACKGROUND

1. Field

The following description relates to a blood pressure monitor including a manually operable pressurizer.

2. Description of Related Art

A sphygmomanometer, or a blood pressure monitor referred to herein, may be an apparatus configured to measure a blood pressure of a user. The blood pressure monitor may apply pressure to a body of a user and measure blood pressure of the user based on values measured while the pressure is being released. Blood pressure monitors typically include a motor to apply the pressure to the body of the user. The blood pressure monitor may transfer or apply, through operation of the motor, pressure to a cuff configured to measure the blood pressure. In addition, the blood pressure monitor may adjust the speed at which the pressure transferred to the cuff is then released.

However, this motor may be large in volume and consume a great amount of power, and thus using such a motor in the blood pressure monitor may not be suitable to reduce the size of the blood pressure monitor. A person's blood pressure may be used to diagnose a disease associated with blood pressure when measured frequently and in various environments.

SUMMARY

This Summary is provided to introduce a selection of concepts in a simplified form that are further described below in the Detailed Description. This Summary is not intended to identify key features or essential features of the claimed subject matter, nor is the Summary intended to be used as an aid in determining the scope of the claimed subject matter.

One or more embodiments include a blood pressure monitor, including a cuff configured to apply a pressure to a target portion of a body of a user, a pressurizer including a rotator, the pressurizer configured to supply a fluid to the cuff, to cause the cuff to apply the pressure, through rotation of the rotator caused by an external rotational force applied to the blood pressure monitor to rotate the rotator, a depressurizer configured to reduce the applied pressure applied by the cuff to the target portion, and a sensor configured to measure a pressure of the target portion.

The pressurizer may include a tube connected to the cuff, and the rotator may be configured to supply the fluid to the cuff by rotating in a state in which at least a portion of the tube is blocked.

The pressurizer may include a string configured to apply the rotational force to rotate the rotator upon an external pulling of the string by the user.

The pressurizer may be a manually operable peristaltic pump operated by the rotation of the rotator.

The pressurizer may include a ratchet configured to selectively maintain a rotation direction to be constant.

The depressurizer may include a rotary damper configured to reduce the pressure applied by the cuff to the target portion at a constant rate by controlling a rotating of the rotator in a direction opposite to the rotation direction of the rotator caused by the external force, when the external force is ceased.

The monitor may further include a tube configured to supply the fluid to the cuff, and the depressurizer may include a valve configured to maintain a speed at which the fluid is discharged from the cuff to be constant when the external rotational force is ceased.

The valve may include a ring configured to obstruct a flow of the fluid, and a support configured to support the ring based on the flow of the fluid and in which a taper, inclined in a direction in which the fluid flows, is formed.

The monitor may further include a controller configured to generate, with respect to a determined change in a blood flow of the target portion, a first feedback signal based on a determination of when pressure should be increased by application of the external force and a second feedback signal based on a determination of when the applied pressure should be decreased.

One or more embodiments provide a blood pressure monitor, including a band configured to cover a target portion of a body of a user and configured to apply pressure to the target portion through movement of a constrictor device of the band, a pressure adjuster configured to cause the band to adjust the movement of the constrictor device to control the applying of the pressure to the target portion, and a sensor configured to measure a pressure of the target portion.

The pressure adjuster may include a support axis winding at least a portion of the band to cause the constrictor device to constrict, and a ratchet configured to selectively maintain a rotation direction of the support axis in a first direction by an external force applied to the blood pressure monitor.

The pressure adjuster may include a rotary damper configured to maintain a rotation speed of the support axis in a second direction at a constant speed when the application of the external force ceases and the ratchet does not maintain the rotation direction of the support axis in the first direction.

The constrictor device may be a string within the band, and the pressure adjuster may include a support axis configured to wind at least a portion of the string to cause the band to constrict in response to an external force applied to the blood pressure monitor, and a ratchet configured to selectively maintain a rotation direction of the support axis in a first direction that winds the string around the support axis.

The pressure adjuster may include a rotary damper configured to maintain a rotation speed of the support axis in a second direction at a constant speed when the application of the external force ceases and the ratchet does not maintain the rotation direction of the support axis in the first direction.

The monitor may further include a controller configured to generate, with respect to a determined change in a blood flow of the target portion, a first feedback signal based on a determination of when pressure should be increased by application of an external force to the pressure adjuster and a second feedback signal based on a determination of when the applied pressure should be decreased.

One or more embodiments provide a blood pressure monitor, including a support system including at least two support elements to at least partially surround a target portion of a body of a user, a pressure adjuster configured to adjust a pressure to be applied to the target portion by the support system by selective control of movement directions of at least one of the two support elements relative to each other, to apply pressure to the target portion by the at least one of the two support elements by being caused, by application of at least one external force to the blood pressure monitor, to move in a respective first movement direction, and a sensor configured to measure a pressure of the target portion.

The pressure adjuster may include a ratchet configured to perform selective control of the at least one of the two support elements to move in the first direction so that an angle between the at least two support elements decreases through the application of the external force.

The pressure adjuster may include at least one hinge damper configured to adjust a speed at which at least one of the two support elements releases to increase an angle between the two support elements at a constant speed to decrease the applied pressure.

The monitor may further include a controller configured to generate, with respect to a determined change in a blood flow of the target portion, a first feedback signal based on a determination of when pressure should be increased by the application of the external force and a second feedback signal based on a determination of when the applied pressure should be decreased.

One or more embodiments provide a blood pressure monitoring method including generating a feedback signal to a user to indicate when a user should cease manual application of an external force to a blood pressure monitor of one or more embodiments discussed herein, measuring pressure of a corresponding target portion of the user based on a determined change in blood flow, and outputting a calculated blood pressure of the user based on measured pressure.

Other features and aspects will be apparent from the following detailed description, the drawings, and the claims.

Figure 1:
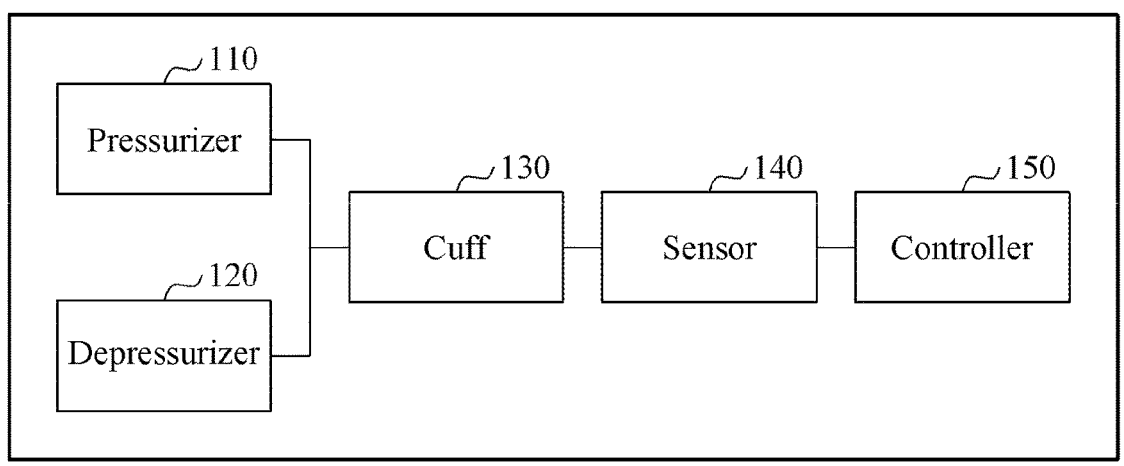
FIG. 1 is a diagram illustrating a blood pressure monitor including a non-powered pressurizer, in accordance with one or more embodiments.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, after an understanding of the present disclosure, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent, after an understanding of the present disclosure, to one of ordinary skill in the art, with the exception of operations necessarily occurring in a certain order. Also, descriptions of functions and constructions that may be understood, after an understanding of differing aspects of the present disclosure, may be omitted in some descriptions for increased clarity and conciseness.

Various alterations and modifications may be made to embodiments, some of which will be illustrated in detail in the drawings and detailed description. However, it should be understood that these embodiments are not construed as limited to the disclosure and illustrated forms and should be understood to include all changes, equivalents, and alternatives within the idea and the technical scope of this disclosure.

Terms used herein are to merely explain specific embodiments, thus it is not meant to be limiting. A singular expression includes a plural expression except when two expressions are contextually different from each other. For example, as used herein, the singular forms "a", "an", and "the" are intended to include the plural forms as well, unless the context clearly indicates otherwise. Herein, a term "include" or "have" are also intended to indicate that characteristics, figures, operations, components, or elements disclosed on the specification or combinations thereof exist. The term "include" or "have" should be understood so as not to pre-exclude existence of one or more other characteristics, figures, operations, components, elements or combinations thereof or additional possibility. In addition, though terms such as first, second, A, B, (a), (b), and the like may be used herein to describe components, unless indicated otherwise, these terminologies are not used to define an essence, order, or sequence of a corresponding component but used merely to distinguish the corresponding component from other component(s).

Unless otherwise defined, all terms including technical and scientific terms used herein have the same meaning as commonly understood by one of ordinary skill in the art to which respective embodiments belong. It will be further understood that terms, such as those defined in commonly-used dictionaries, should be interpreted as having a meaning that is consistent with their meaning in the context of the relevant art and the present disclosure and will not be interpreted in an idealized or overly formal sense unless expressly so defined herein.

When describing the examples with reference to the accompanying drawings, like reference numerals refer to like constituent elements and a repeated description related thereto will be omitted. When it is determined that a detailed description related to an understood or previously discussed operation or configuration may make a purpose of a subsequent embodiment unnecessarily ambiguous in describing the embodiment, such a detailed description will be omitted.

As only an example, in the field of wearable devices such as smart watches and smartwear, the size and power consumption of a blood pressure monitor may be an important issue to be considered. Accordingly, in one or more embodiments, a blood pressure monitor with a reduced size and reduced power requirements may be provided. For example, the blood pressure monitor may be configured so that pressurization may be implemented with a non-powered pressurizer that operates based on manual pressure inducements with a reduced size for compact use, such as with smart watch or smart wear embodiments, as well as with other embodiments.

FIG. 1 is a diagram illustrating a blood pressure monitor 100 including a non-powered pressurizer, in accordance with one or more embodiments. Referring to FIG. 1, the blood pressure monitor 100 includes a pressurizer 110, a depressurizer 120, a cuff 130, a sensor 140, and a controller 150, for example. The blood pressure monitor 100 measures a blood pressure of a user from a target portion of a body of the user. The target portion may include, for example, a wrist and an upper arm of the user. The target portion may be, for example, an entire wrist and an entire upper arm of the user. The target portion may be, for example, a portion of the wrist and a portion of the upper arm of the user. The target portion may be, for example, a portion of the wrist and the upper arm in which an artery passes. For example, the target portion may be a portion in which a radial artery and brachial artery of the user pass.

The pressurizer 110 is configured to increase a pressure that is applied to the target portion. The pressurizer 110 increases the pressure for the target portion by an external force. The external force may be generated through manipulation by the user. Depending on embodiment, the pressurizer 110 may increase the pressure for the target portion through various mechanisms based on an external force. In a non-limiting example, the pressurizer 110 may increase the pressure for the target portion by supplying a fluid to the cuff 130 through rotation by an external force. In another non-limiting example, the pressurizer 110 may increase the pressure for the target portion through a contraction of a band covering the target portion. In still another non-limiting example, the pressurizer 110 may increase the pressure for the target portion through a tightening of the band covering the target portion. In yet another non-limiting example, the pressurizer 110 may increase the pressure for the target portion through a tightening of a support of a support system configured to support the target portion. Further descriptions of such examples will be described in greater detail further below.

The depressurizer 120 is configured to reduce the pressure that is applied to the target portion. The depressurizer 120 may start a depressurizing of the target portion by an external force. After the depressurizing of the target portion starts by the external force, a depressurization state may be maintained by a structure of the depressurizer 120. To measure an accurate blood pressure, maintaining a depressurization speed may be desired. The depressurization speed indicates a rate at which a pressure is reduced per hour, for example. The depressurizer 120 may include various structures to maintain the depressurization speed. In an example, the depressurizer 120 may include various dampers. For example, the depressurizer 120 may include at least one of a rotary damper and a hinge damper. In another example, the depressurizer 120 may include various valves. For example, the depressurizer 120 may include a constant flow valve. Such example structures will be described in greater detail further below, noting that alternative embodiments are also available.

In a case that the pressure of the target portion increases and decreases through any one structure, the pressurizer 110 and the depressurizer 120 may be referred to as a pressure adjuster.

The cuff 130 applies a pressure to the target portion. The cuff 130 may include, or caused to include, various fluids to allow the cuff 130 to be closely attached to the target portion. A fluid may include various forms of gas and liquid. For example, the fluid may include air and a gel. For example, a degree of contact between the cuff 130 and the target portion may be adjusted based on an amount of the fluid included in the cuff 130. In one or more embodiments, the cuff 130 may be provided as a flexible material to be in a closer contact with the target portion.

The sensor 140 measures a pressure of the target portion. In addition, the sensor 140 may measure a blood flow of the target portion. The sensor 140 may be located around the target portion. The sensor 140 may include a pressure sensor configured to measure the pressure of the target portion and an optical sensor configured to measure the blood flow of the target portion, for example.

The controller 150 may generate measurement data based on an output data, readings, or signals from the sensor 140. The measurement data may include a blood pressure in a contraction period, a mean blood pressure, and a blood pressure in a relaxation period, for example. A process of calculating the blood pressure in the contraction period, the mean blood pressure, and the blood pressure in the relaxation period will be described in greater detail further below.

In addition, the controller 150 may generate diagnosis data based on the measurement data. For example, the controller 150 may generate the diagnosis data by comparing the measurement data to reference data. The diagnosis data may include data or conclusions regarding a health condition of the user associated with a blood pressure. For example, the controller 150 may determine whether the blood pressure of the user is normal, high, or low by comparing the measurement data to the reference data. The reference data may be determined based on physical information of the user. For example, the reference data may be determined to be data corresponding to the physical information of the user among various sets of data corresponding to various sets of physical information. The controller 150 may include an input user interface, for example, where such reference information or other information is entered for consideration by the controller 150.

The controller 150 may be configured to transmit at least one of the measurement data and the diagnosis data to an external device, for example. In an embodiment, the external device may include a personal device of the user and a medical server, such as in a blood monitoring system embodiment. In an embodiment, the controller 150 may be configured to transmit the measurement data and the diagnosis data to the personal device of the user to allow the user to verify the measurement data and the diagnosis data through the personal device of the user. Also, the controller 150 may be configured to transmit the measurement data to the medical server. In an embodiment, a doctor may input the diagnosis data to the medical server based on the measurement data, and the controller 150 may be configured to then receive the diagnosis data from the medical server.

The controller 150 may be configured to generate a feedback signal, e.g., associated with a desired manipulation by the user. For example, the feedback signal may include a first feedback signal to request the user for pressurization and a second feedback signal to request the user for depressurization. A process of generating the feedback signal will be described in greater detail further below.

Here, the controller 150 includes hardware that may be configured to implement one or more, or all, of the operations described herein, depending on embodiment. As only an example, the hardware may be a special purpose processor or computer, e.g., configured to implement one or more methods or operations described herein and/or configured to implement or operate based on processor readable code that implements such methods or operations.

Although not illustrated in FIG. 1, depending on embodiment, the blood pressure monitor 100 includes an output device component. The output device component is a hardware component that may include at least one of a display device, a speaker, and a vibrator, as only examples. The controller 150 may output the feedback signal to the user through the output device component. In addition, the controller 150 may output the measurement data and the diagnosis data to the user through the output device component. In addition, depending on embodiment, the controller 150 or the blood pressure monitor 100 includes one or more input device components, as hardware that are configured to request, accept, or receive input from a user interface and/or signals of sensors of the blood pressure monitor 100 or external sensors of the blood pressure monitor, such as for measuring pressure or blood flow, as discussed in greater detail further below.

Still further, although not illustrated in FIG. 1, in one or more embodiments, the blood pressure monitor 100 includes a communication hardware module. For example, the controller 150 exchanges the data with the personal device of the user and the medical server through the communication module.

Figure 2:
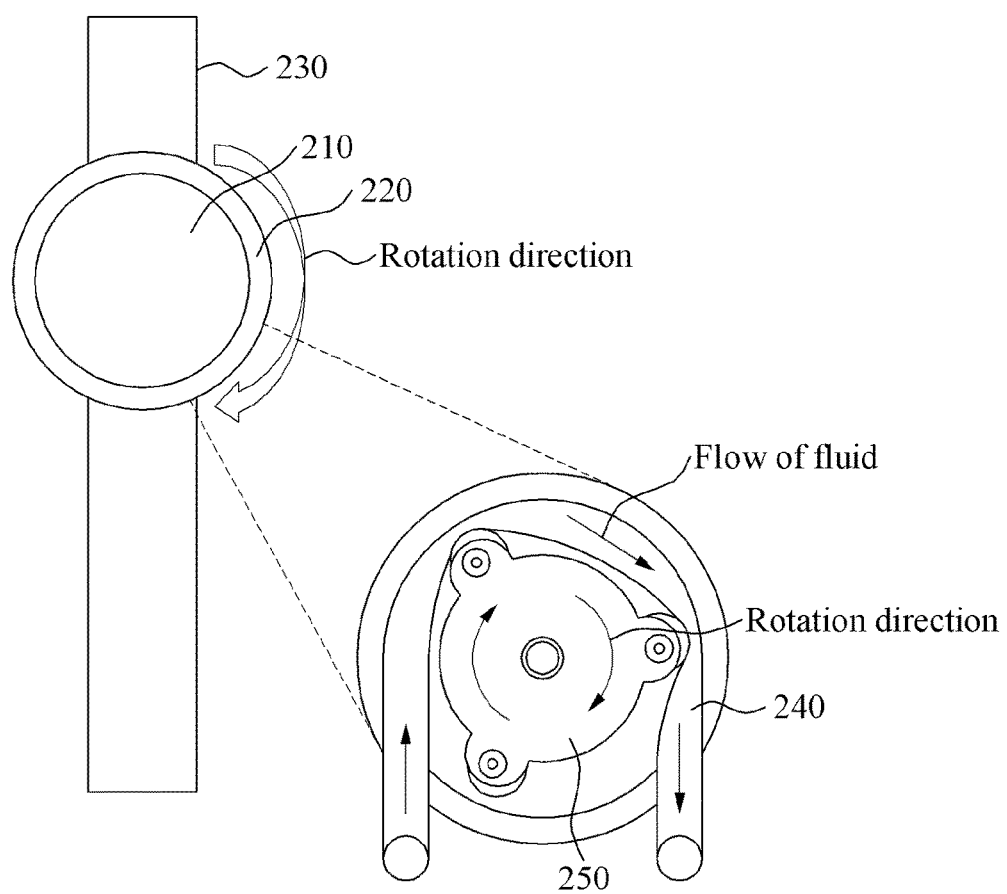
FIG. 2 is a diagram illustrating a blood pressure monitor configured to adjust pressure applied to a target portion using a fluid, in accordance with one or more embodiments.

FIG. 2 is a diagram illustrating a blood pressure monitor configured to adjust pressure applied to a target portion using a fluid, in accordance with one or more embodiments. Referring to FIG. 2, the blood pressure monitor may include a body 210, a bezel 220, a band 230, a tube 240, and a rotator 250, for example. The blood pressure monitor may also include the cuff 130, the sensor 140, and the controller 150, for example, described with reference to FIG. 1.

In one or more embodiments, the body 210 is fixed to the band 230, for example. The body 210 includes at least a portion of the tube 240 and the rotator 250. The bezel 220 rotates on the body 210 through an external force. The bezel 220 rotates the rotator 250 based on the external force.

The tube 240 and the rotator 250 are collectively referred to as a pressurizer. The tube 240 and the rotator 250 supply a fluid to a cuff through rotation by an external force. For example, the tube 240 and the rotator 250 may be a peristaltic pump, and the tube 240 and the rotator 250 may make up a manually operable peristaltic pump, as only an example of such a manually operable peristaltic pump.

In one or more embodiments, one end of the tube 240 is connected to the cuff, and another end of the tube 240 is connected to a fluid bag to supply the fluid or is exposed in air. For example, the other end of the tube 240 may be disconnected. A hole may be present around the other end of the tube 240. The tube 240 is connected to the cuff through the band 230. The fluid included in the tube 240 flows through the rotation of the rotator 250. The tube 240 supplies the fluid to the cuff through the rotation of the rotator 250.

The rotator 250 may include a plurality of projections. The projections may form a plurality of spaces in the tube 240. Thus, the rotator 250 may block at least a portion of the tube 240. Here, to "block" and to perform a "blocking" as referred to herein may be construed as indicating a state that may induce a flow of the fluid rather than indicating closing or sealing. The rotator 250 supplies the fluid to the cuff while rotating in a state in which the at least a portion of the tube 240 is blocked. The rotator 250 rotates in a rotation direction as illustrated in FIG. 2. In one or more embodiments, the rotator 250 includes a ratchet. The rotation direction of the rotator 250 may be maintained by application of the ratchet. A discharge of the fluid supplied to the cuff may be prevented through the ratchet. A lock of the ratchet may be released by an external force, for example. When the lock of the ratchet is released, depressurization of the target portion may be initiated. For example, when the lock of the ratchet is released, the rotator 250 may be connected to a rotary damper.

Thus, in one or more embodiments, the band 230 fixes the blood pressure monitor to a body of a user. The band 230 fixes the cuff. The cuff is fixed to the target portion through the band 230. An example of the cuff will be described in greater detail with reference to FIG. 3.

Here, though a blood pressure monitor configured to adjust pressure applied to a target portion using a fluid has been discussed above with reference to elements of FIG. 2, embodiments are not limited thereto and alternative manually operable fluid based pressure inducing elements may be used for applying pressure to the target portion.

Figure 3:
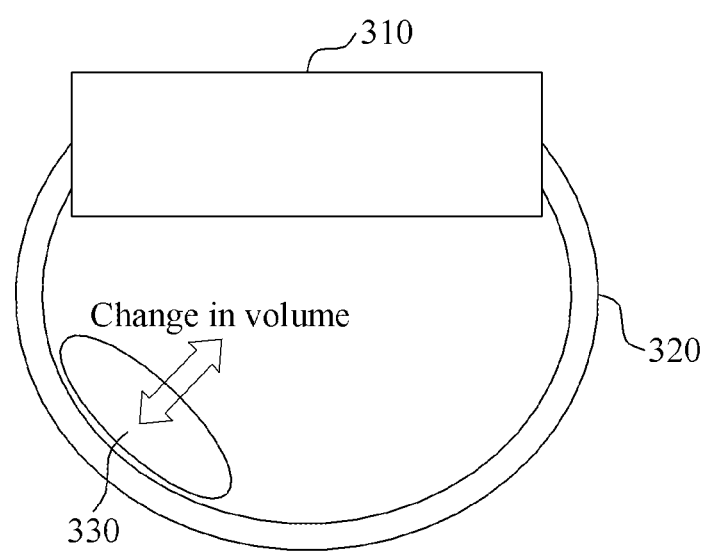
FIG. 3 is a diagram illustrating a blood pressure monitor cuff, in accordance with one or more embodiments.

FIG. 3 is a diagram illustrating a blood pressure monitor cuff 330, in accordance with one or more embodiments. Referring to FIG. 3, a blood pressure monitor includes a body 310, a band 320, and the cuff 330. The blood pressure monitor may also include the bezel 220, the tube 240, and the rotator 250, such as described with reference to FIG. 2. For example, the body 310 may include the tube 240 and the rotator 250.

The cuff 330 may be provided in various sizes based on the target portion. The cuff 330 may be provided in a size to apply a pressure to a portion around a radial artery. For example, the cuff 330 may be provided in a size corresponding to a portion of the band 320. Also, the cuff 330 may be provided in a size to apply a pressure to an entire portion of a wrist. For example, the cuff 330 may be provided in a size corresponding to an entire portion of the band 320.

The cuff 330 includes a fluid to be closely attached to the target portion. A volume of the cuff 330 may vary with the fluid. The cuff 330 is connected to a tube, for example, the tube 240. An amount of the fluid included in the cuff 330 is adjusted through the tube. For example, the fluid may be supplied to the cuff 330 through the tube, and discharged from the cuff 330 through the tube. The cuff 330 is expanded by the supply of the fluid, and contracted by the discharge of the fluid. That is, the cuff 330 may increase a pressure of the target portion by the supply of the fluid, and decrease the pressure of the target portion by the discharge of the fluid.

Referring back to FIG. 2, the rotator 250 rotates by an external force. The external force may include manipulation by the user. In an example, the rotator 250 may rotate through a string. Such a string will be further described with reference to FIG. 4, as only an example.

Figure 4:
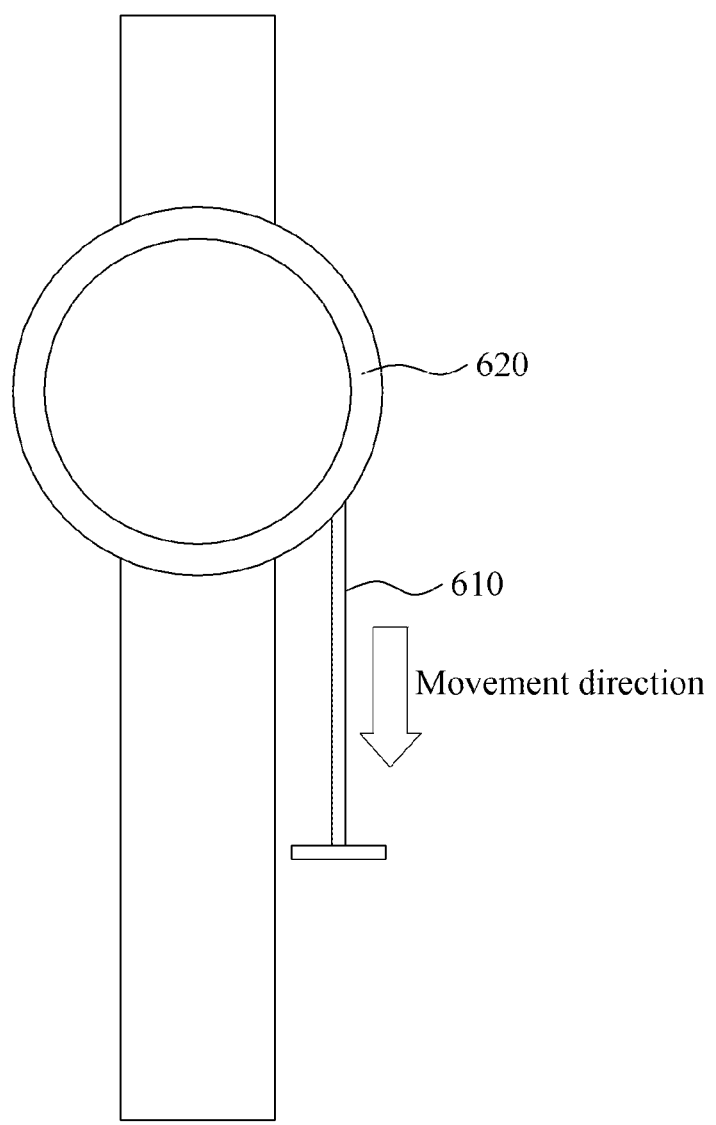
FIG. 4 is a diagram illustrating a blood pressure monitor with a string for rotation of a rotator, in accordance with one or more embodiments.

FIG. 4 is a diagram illustrating a blood pressure monitor with a string 610 for rotation of a rotator, in accordance with one or more embodiments. Referring to FIG. 4, a blood pressure monitor includes the string 610 and a bezel 620. The string 610 is connected to the bezel 620. The string 610 may be connected to the bezel 620 or the rotator 250, such as described with reference to FIG. 2. In an embodiment, when the string 610 is pulled in a movement direction as illustrated in FIG. 4, the bezel 620 or the rotator 250 may rotate clockwise, for example. Thus, a user may increase a pressure of a target portion using the string 610 without directly manipulating the bezel 620.

Referring back to FIG. 2, for example, the rotator 250 supplies a fluid to a cuff while rotating in a rotation direction as illustrated in FIG. 2. In addition, the rotator 250 may discharge the fluid supplied to the cuff while rotating in a direction opposite to the rotation direction. In response to the discharge of the fluid, a pressure of the target portion may decrease. To measure an accurate blood pressure, a depressurization speed may need to be maintained. The depressurization speed may be maintained using various structures. The depressurization speed may be maintained using various dampers. For example, the depressurization speed may be maintained using a rotary damper. Alternatively, the depressurization speed may be maintained using a valve. Such a rotary damper and valve will be further respectively described with reference to FIGS. 5 and 6, as only examples.

Here, though a blood pressure monitor configured to adjust pressure applied to a target portion using a string has been discussed above with reference to elements of FIG. 4, embodiments are not limited thereto and alternative manual devices other than such a string may be used for externally rotating the bezel or rotator.

Figure 5:
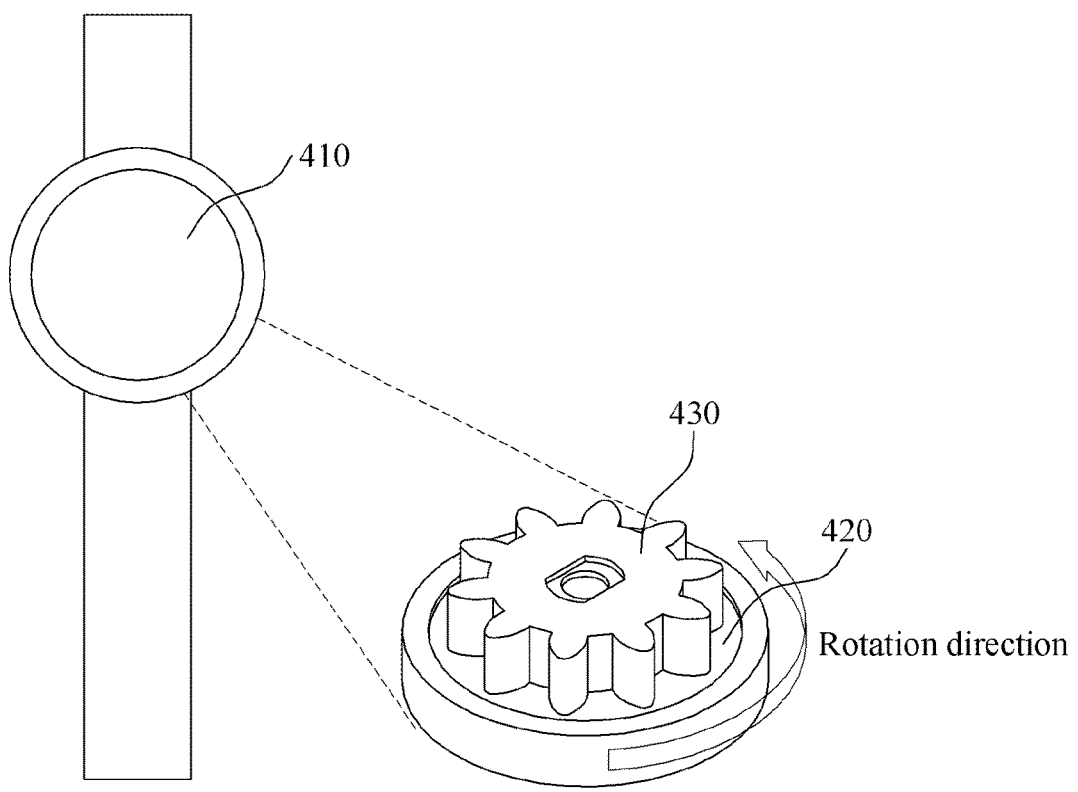
FIG. 5 is a diagram illustrating a blood pressure monitor with a rotary damper, in accordance with one or more embodiments.

FIG. 5 is a diagram illustrating a blood pressure monitor with a rotary damper, in accordance with one or more embodiments. Referring to FIG. 5, a blood pressure monitor includes a body 410, a support 420, and a rotator 430, for example. The blood pressure monitor may also include the bezel 220, the tube 240, and the rotator 250, such as described with reference to FIG. 2. For example, the body 410 may include at least a portion of the tube 240 and the rotator 250. The support 420 and the rotator 430 may be collectively referred to as a depressurizer.

The body 410 includes the support 420 and the rotator 430. In one or more embodiments, the support 420 is fixed to the body 410. The rotator 430 rotates on the support 420 in a rotation direction as illustrated in FIG. 5. A rotation speed of the rotator 430 may be maintained to be constant through friction with the support 420. For example, the rotation speed of the rotator 430 may be maintained to be constant by a lubricant between the rotator 430 and the support 420 or a spring connecting the rotator 430 and the support 420.

The rotator 430 may be connected to the rotator 250, such as illustrated in FIG. 2. For example, when a lock of a ratchet is released, the rotator 430 may be connected to the rotator 250 through an axis of the support 420. The rotator 430 and the rotator 250 may share the axis and be located on opposite sides of the support 420. The rotator 430 may maintain a rotation speed of the rotator 250. For example, the rotator 430 may maintain the depressurizing rotation speed of the rotator 250 to be constant through friction with the support 420. In response to the rotation speed of the rotator 250 being maintained, a depressurization speed of a target portion may be maintained. Thus, accuracy in measuring a blood pressure may be improved.

Figure 6:
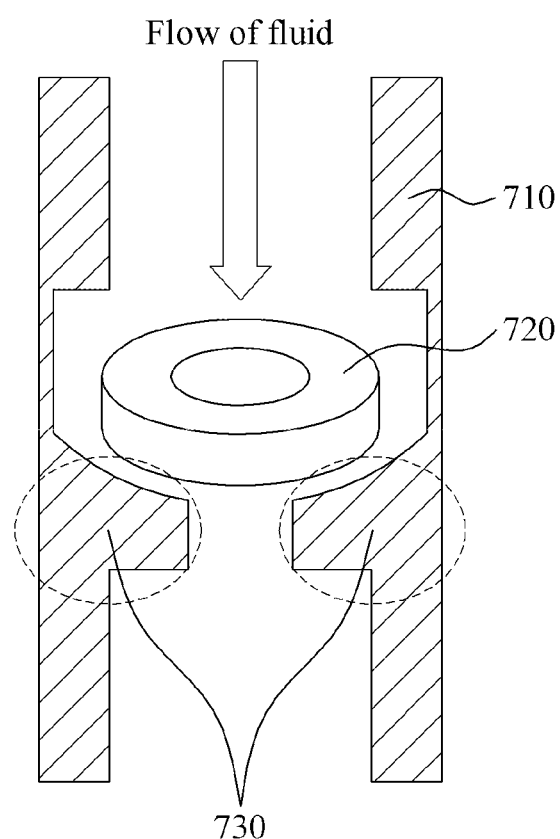
FIG. 6 is a diagram illustrating a valve configured to maintain a depressurization speed, in accordance with one or more embodiments.

FIG. 6 is a diagram illustrating a valve configured to maintain a depressurization speed, in accordance with one or more embodiments. Referring to FIG. 6, a tube 710 may include a ring 720 and a support 730, for example. The tube 710 may be a portion of the tube 240, such as described with reference to FIG. 2.

The ring 720 may obstruct a flow of a fluid through a hole smaller than the tube 710. The ring 720 may move in a direction in which the fluid flows based on the flow of the fluid. The ring 720 may be closely attached to the support 730 based on a speed of the fluid. The support 730 may include a taper inclined in the direction in which the fluid flows. When the ring 720 is attached closer to the support 730, the hole of the ring 720 may be narrowed. Also, when the ring 720 is attached closer to the support 730, the speed of the fluid may decrease. Thus, the speed of the fluid may be maintained to be constant through the ring 720 and the support 730, and thus accuracy in measuring a blood pressure may be improved.

Figure 7:
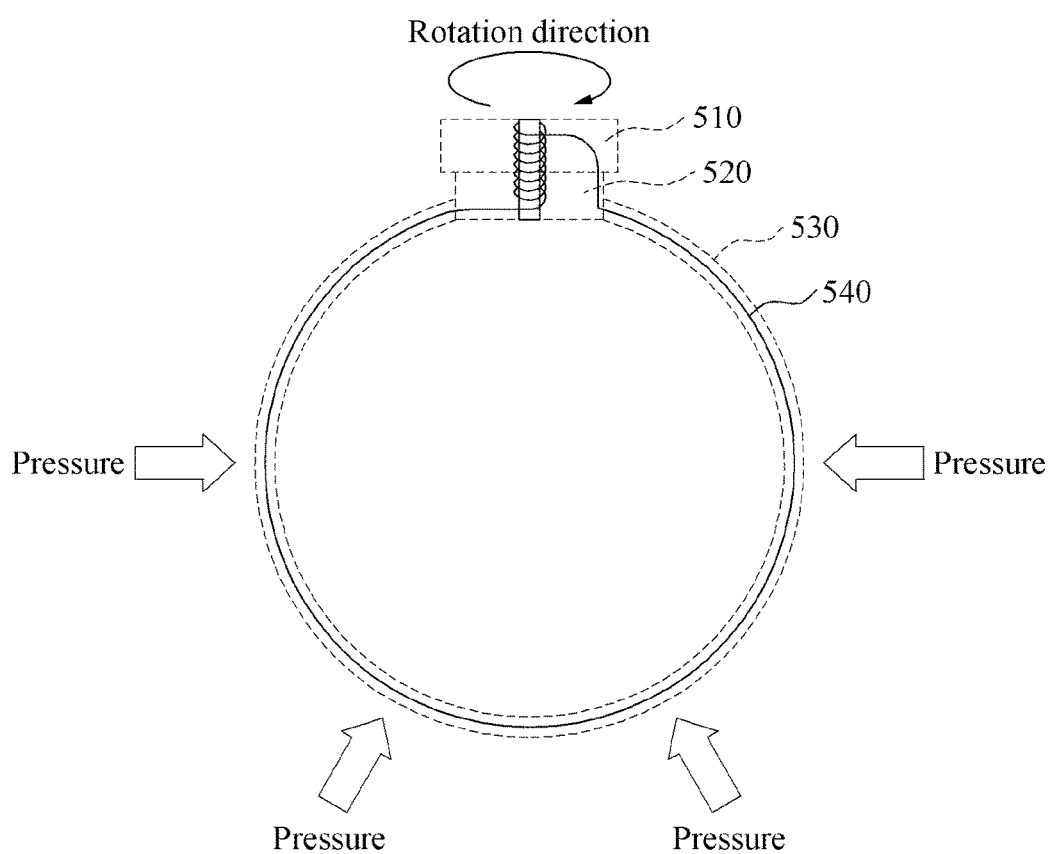
FIG. 7 is a diagram illustrating a blood pressure monitor configured to adjust pressure applied to a target portion through a contraction of a band, in accordance one or more embodiments.

FIG. 7 is a diagram illustrating a blood pressure monitor configured to adjust pressure applied to a target portion through a contraction of a band 530, in accordance with one or more embodiments. Referring to FIG. 7, the blood pressure monitor may include a rotator 510, a body 520, the band 530, and a string 540, for example. The blood pressure monitor may also include the cuff 130, the sensor 140, and the controller 150, such as described with reference to FIG. 1.

The string 540 may be wound around a support axis fixed to the rotator 510 when the rotator 510 rotates in a rotation direction as illustrated in FIG. 7. At least a portion of the band 530 may include a cuff, for example, the cuff 130. When the string 540 is wound around the support axis, the band 530 may be contracted. In response to the band 530 being contracted, the pressure of the target portion may increase. When the string 540 is released from the support axis, the band 530 may be relaxed. In response to the band 530 being relaxed, the pressure of the target portion may decrease. The body 520 may include a ratchet configured to adjust a rotation direction of the support axis to allow the support axis to rotate in a constant direction.

A relaxation speed of the band 530 may be adjusted by at least one damper described in the foregoing. For example, the rotation speed of the support axis may be adjusted by a rotary damper. As described in the foregoing, the rotation speed of the support axis may be maintained to be constant through friction between a rotator of the rotary damper and a support of the rotary damper or by a spring connecting the rotator of the rotary damper and the support of the rotary damper. The string 540, the support axis, and the ratchet may be collectively referred to a pressure adjuster.

Here, though a blood pressure monitor configured to adjust pressure applied to a target portion using elements for contracting a band have been discussed above with reference to elements of FIG. 7, embodiments are not limited thereto and alternative elements for adjusting the pressure may be used.

Figure 8:
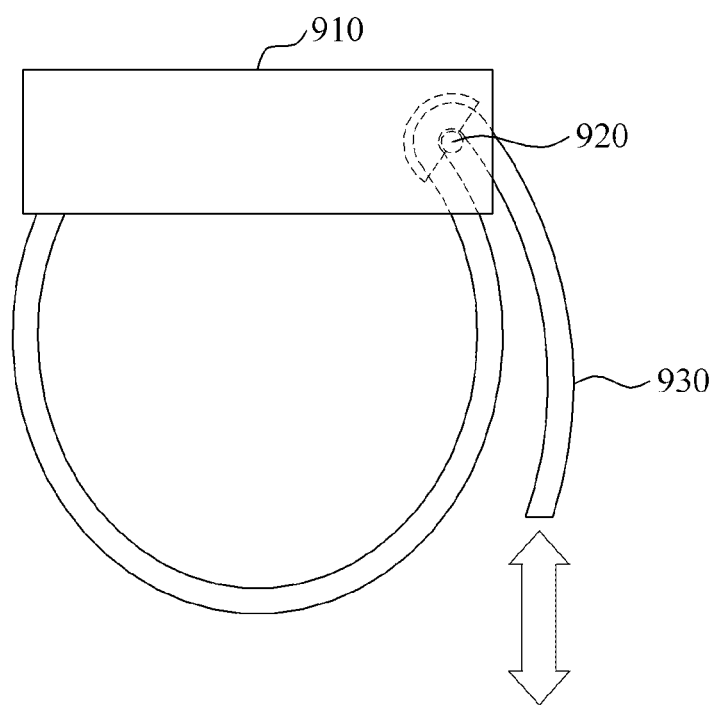
FIG. 8 is a diagram illustrating a blood pressure monitor configured to adjust pressure applied to a target portion through a tightening of a band, in accordance one or more embodiments.

FIG. 8 is a diagram illustrating a blood pressure monitor configured to adjust pressure applied to a target portion through a tightening of a band 930, in accordance with one or more embodiments. Referring to FIG. 8, the blood pressure monitor may include a body 910, a pressure adjuster 920, and the band 930, for example. The blood pressure monitor may also include the cuff 130, the sensor 140, and the controller 150, such as described with reference to FIG. 1.

In one or more embodiments, the body 910 includes the pressure adjuster 920. The pressure adjuster 920 may include a support axis covering at least a portion of the band 930. In addition, the pressure adjuster 920 may include a ratchet configured to adjust a rotation direction of the support axis to allow the support axis to rotate in a constant direction through an external force. In response to a movement of the band 930 in an arrow-indicating direction as illustrated in FIG. 8, a pressure to be applied to the target portion may be adjusted. For example, when the support axis rotates in a first direction, the pressure of the target portion may increase. When the support axis rotates in a second direction, the pressure of the target potion may decrease. A user may increase the pressure of the target portion by pulling the band 930, and decrease the pressure of the target portion by releasing the band 930.

A depressurization speed may be determined based on a speed at which the band 930 is released. The speed at which the band 930 is released may be adjusted based on the user manually controlled rotation speed of the support axis. For example, the rotation speed of the support axis in the second direction may be maintained to be constant through a rotary damper. As described in the foregoing, the rotation speed of the support axis may be maintained to be constant through friction between a rotator of the rotary damper and a support of the rotary damper or by a spring connecting the rotator of the rotary damper and the support of the rotary damper, as only examples.

Here, though a blood pressure monitor configured to adjust pressure applied to a target portion using elements for tightening a band have been discussed above with reference to elements of FIG. 8, embodiments are not limited thereto and alternative elements for tightening the band may be used.

Figure 9:
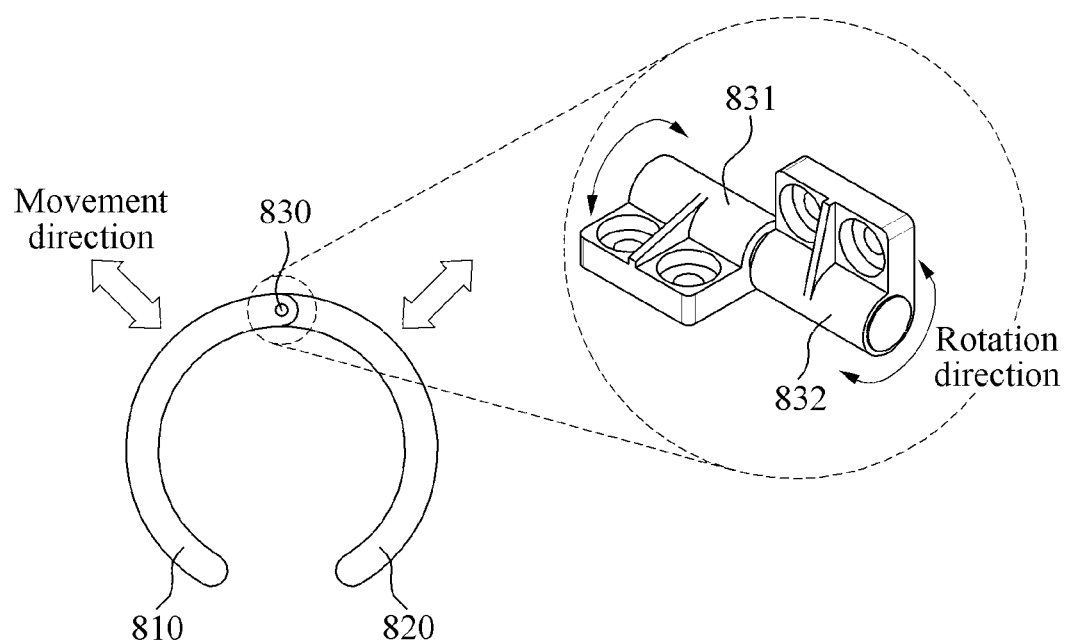
FIG. 9 is a diagram illustrating a blood pressure monitor configured to adjust pressure applied to a target portion through a tightening of a support, in accordance with one or more embodiments.

FIG. 9 is a diagram illustrating a blood pressure monitor configured to adjust pressure applied to a target portion through a tightening of a support, in accordance with one or more embodiments. Referring to FIG. 9, the blood pressure monitor may include a first support 810, a second support 820, and a pressure adjuster 830, for example. The blood pressure monitor may also include the cuff 130, the sensor 140, and the controller 150, such as described with reference to FIG. 1.

The first support 810 and the second support 820 may cover the target portion. Depending on embodiment, the first support 810 and the second support 820 may cover the entirety of the target portion, such as completely surrounding a wrist or arm body portion, or may cover only a portion of the target portion. The first support 810 and the second support 820 cover the target portion by being tightened or closed in an arrow-indicating direction as illustrated in FIG. 9. Thus, an angle between the first support 810 and the second support 820 may be adjusted through an external force.

The pressure adjuster 830 may include a ratchet, for example, configured to adjust a direction in which the first support 810 and the second support 820 are tightened to allow the angle between the first support 810 and the second support 820 to decrease. For example, the ratchet may maintain a direction in which the first support 810 and the second support 820 move to decrease the angle between the first support 810 and the second support 820 to reach a limit angle. In response to the decrease in the angle between the first support 810 and the second support 820, the pressure of the target portion may increase.

When the ratchet is released, the angle between the first support 810 and the second support 820 may increase. In response to the increase in the angle between the first support 810 and the second support 820, the pressure of the target portion may decrease. A depressurization speed may be determined based on a speed at which the angle between the first support 810 and the second support 820 increases. The pressure adjuster 830 includes hinge dampers, for example, a first hinge damper 831 and a second hinge damper 832, configured to adjust the speed at which the supports 810 and 820 are released to allow the angle between the first support 810 and the second support 820 to increase at a constant speed. The first hinge damper 831 may be fixed to the first support 810, and the second hinge damper 832 may be fixed to the second support 820, for example. When the depressurization speed is maintained by the hinge dampers 831 and 832, accuracy in measuring a blood pressure may be improved.

Here, though a blood pressure monitor configured to adjust pressure applied to a target portion using a support system that can be tightened have been discussed above with reference to elements of FIG. 9, embodiments are not limited thereto and alternative support system support elements that can be tightened, clamped, or closed relative to each other, for example, may be used.

Figure 10A:
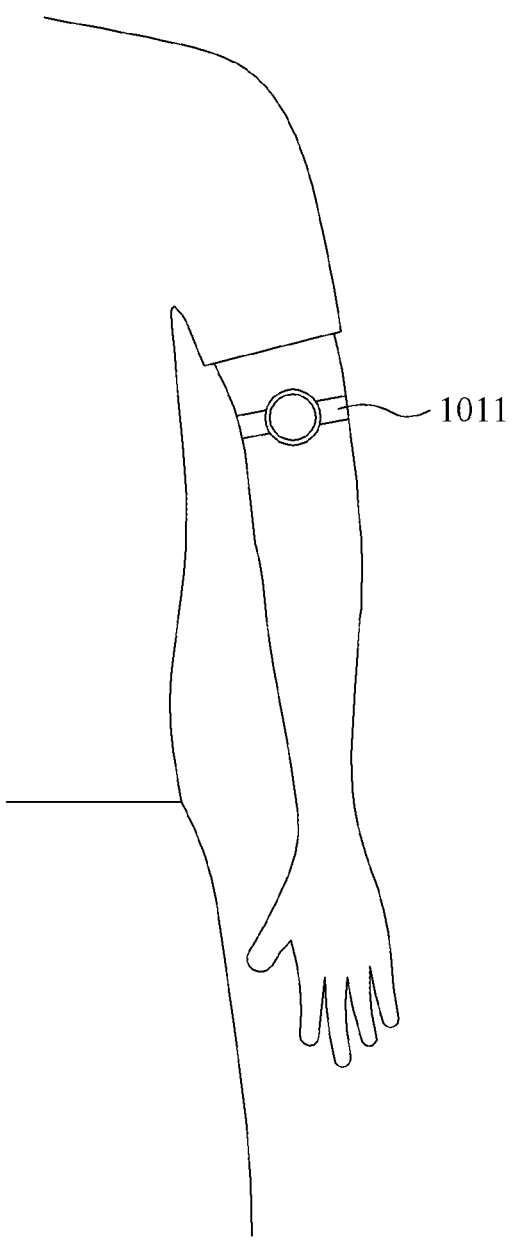
FIGS. 10A and 10B illustrate examples of states in which a blood pressure monitor may be worn, in accordance with one or more embodiments.
Figure 10B:
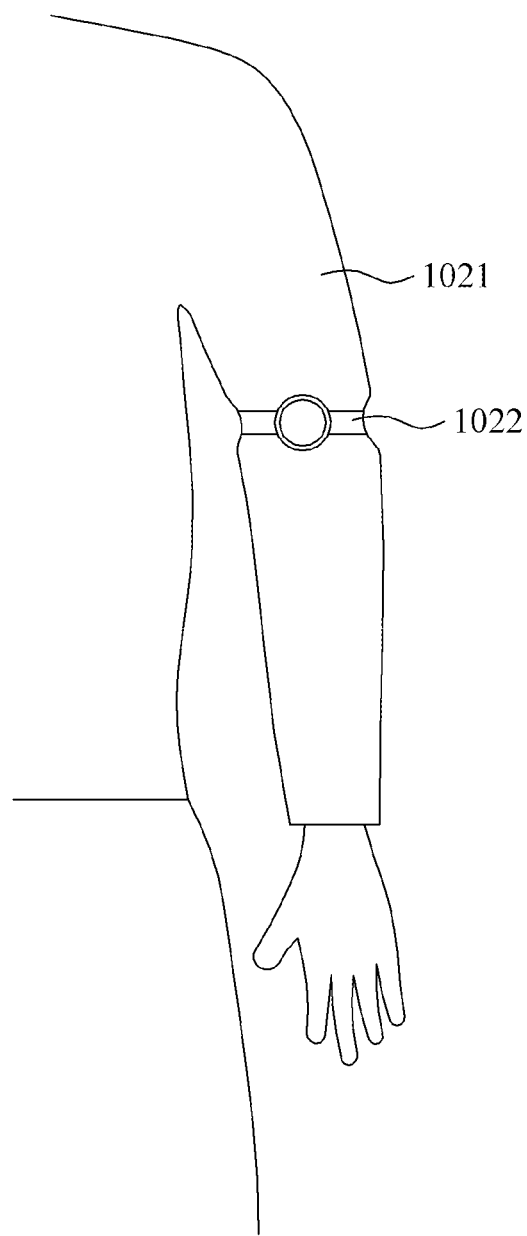

FIGS. 10A and 10B illustrate examples of states in which a blood pressure monitor may be worn, in accordance with one or more embodiments. Referring to FIG. 10A, a blood pressure monitor 1011 is worn around an upper arm of a user. The blood pressure monitor 1011 includes an expandable band to be worn on various portions of a body of the user. Referring to FIG. 10B, a blood pressure monitor 1022 is included in a smartwear device 1021. A user may measure a blood pressure through the blood pressure monitor 1022 while the user is wearing the smartwear device 1021.

Figure 11:
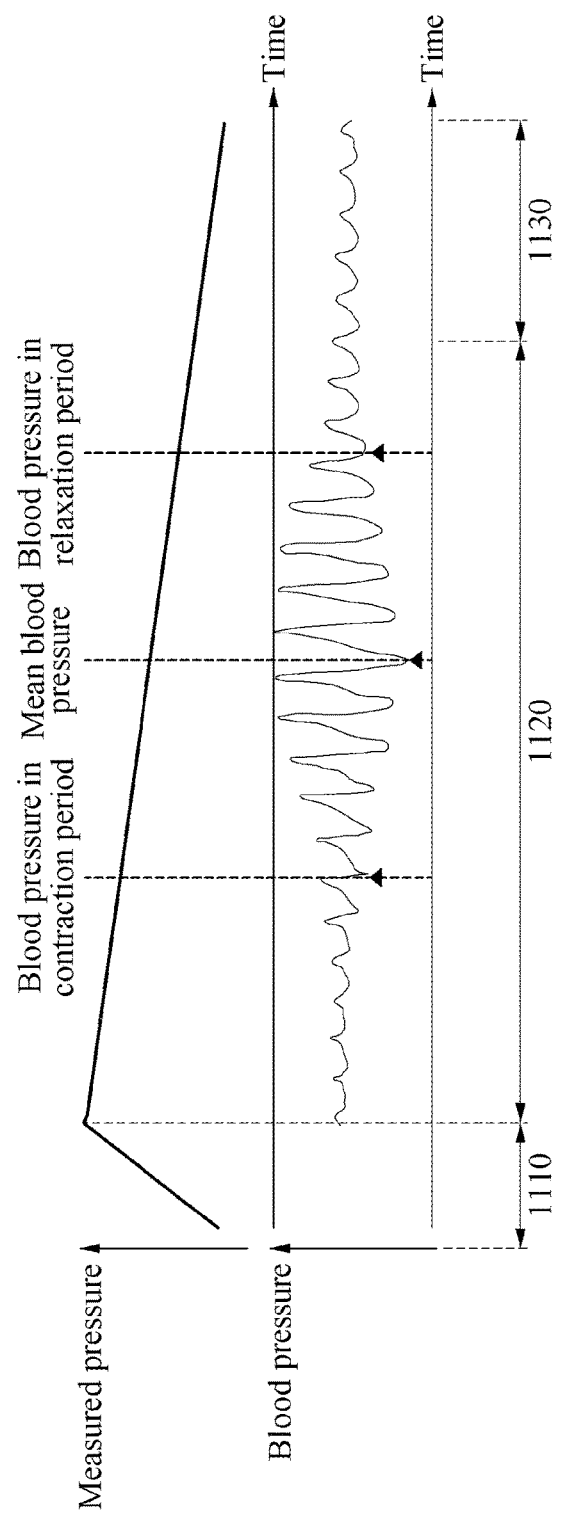
FIG. 11 is a graph illustrating an operation of a controller of a blood pressure monitor, in accordance with one or more embodiments.

FIG. 11 is a graph illustrating an operation of a controller of a blood pressure monitor, in accordance with one or more embodiments.

In the graph of FIG. 11, a pressure measured in a first section 1110, a second section 1120, and a third section 1130, and an actual blood pressure of a user are illustrated. The first section 1110 is a section in which an increase in a pressure by an external force is manually made by the user, the second section 1120 is a section in which a decrease in the pressure is made, and the third section 1130 is a section in which measurement data and diagnosis data are generated based on measured pressures.

In the first section 1110, a first feedback signal may be output to request the user to apply pressure. The user may create and increase pressure applied to a target portion through a blood pressure monitor based on the first feedback signal. For example, the user may rotate the bezel 220 illustrated in FIG. 2. In the second section 1120, a second feedback signal may be output to request the user to reduce the applied pressure. The user may decrease the pressure of the target portion through the blood pressure monitor based on the second feedback signal. For example, the user may release a lock of a ratchet by touching the body 210 illustrated in FIG. 2. The first feedback signal and the second feedback signal may be output through an output device component of the blood pressure monitor, such as discussed above, or an external device.

In the third section 1130, the measurement data and the diagnosis data are generated based on the measured pressure. The measurement data and the diagnosis data may be generated by the controller 150, such as described with reference to FIG. 1. In response to the pressure of the target portion being lowered, a pulsation may be detected in the target portion. The controller determines a pressure at which the pulsation is detected to be a blood pressure in a contraction period. For example, the controller determines a pressure at which an amplitude of the pulsation is at a maximum level to be a mean blood pressure. In addition, the controller determines a pressure at which the pulsation decreases to a minimum level to be a blood pressure in a relaxation period, for example.

Figure 12:
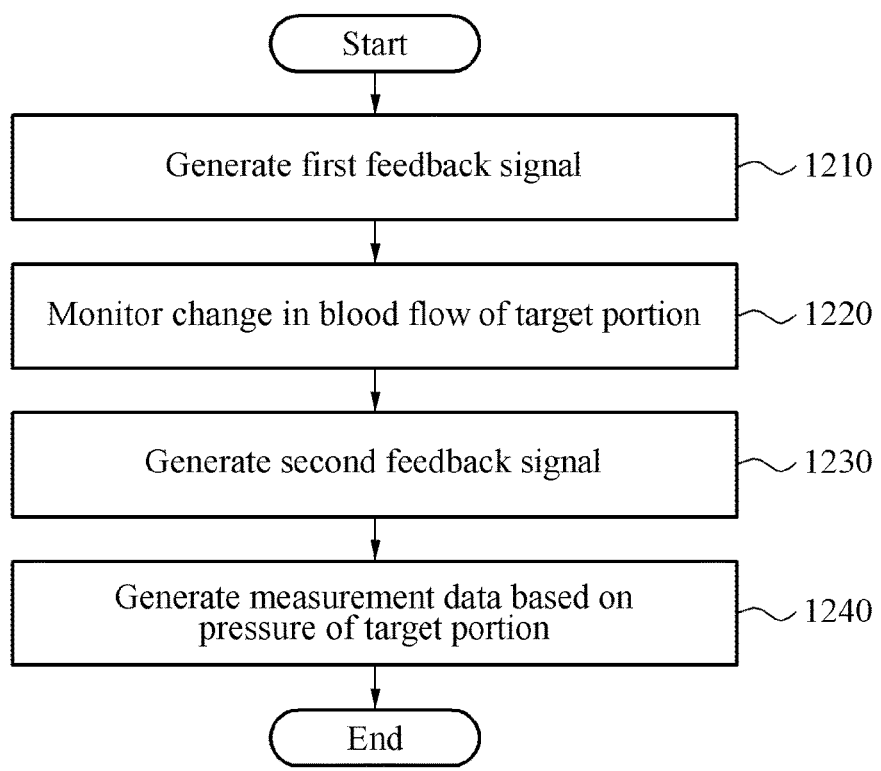
FIG. 12 is a flowchart illustrating controller operations in a blood pressure monitoring method, in accordance with one or more embodiments.

FIG. 12 is a flowchart illustrating controller operations in a blood pressure monitoring method, in accordance with one or more embodiments. Referring to FIG. 12, in operation 1210, the controller generates a first feedback signal. The first feedback signal is a signal to request a user to apply pressure. The controller outputs the first feedback signal to the user. In operation 1220, the controller monitors a change in a blood flow of a target portion. In operation 1230, the controller generates a second feedback signal. The second feedback signal is a signal to request the user to reduce the pressure. The controller may generate the second feedback signal after verifying whether the blood flow of the target portion is suspended in response to the pressure being applied to the target portion. The controller outputs the second feedback signal to the user. In operation 1240, the controller generates measurement data based on measured pressures of the target portion. The measurement data may include, for example, measurements of blood pressures during a contraction period, a determined mean blood pressure, and measurements of blood pressure during a relaxation period. The controller generates diagnosis data based on the measurement data. In addition, in one or more embodiments, the controller transmits the measurement data and the diagnosis data to an external device, or outputs the data to the user through an output device component, such as discussed above.

The apparatuses, units, modules, devices, and other components illustrated in any of the blood pressure monitors of FIGS. 1 through 10B that perform the operations of FIGS. 11-12, for example, are implemented by hardware components. As only an example, the controllers of any of the blood pressure monitors of FIGS. 1-10B include such hardware components. Hardware components may include, as only examples, resistors, transistors, capacitors, inductors, power supplies, controllers, frequency generators, operational amplifiers, power amplifiers, low-pass filters, high-pass filters, band-pass filters, analog-to-digital converters, digital-to-analog converters, and processing device(s), processor(s), and/or computer(s), as only examples. A processing device, processor, or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processing device, processor, or computer includes, or is connected to, one or more memories storing instructions or software that are executed by the processing device, processor, or computer and that may control the processing device, processor, or computer to implement one or more methods described herein. Hardware components implemented by a processing device, processor, or computer, such as of the controller of any of the blood pressure monitors of FIGS. FIGS. 1-10B, as only an example, may execute instructions or software, such as an operating system (OS) and one or more software applications that run on the OS, to perform or control one or more of the operations described herein with respect to FIGS. 11-12, for example. The hardware components also access, manipulate, process, create, and/or store data in response to execution of the instructions or software. For simplicity, the singular term "processing device", "processor", or "computer" may be used in the description of the examples described herein, but in other examples multiple processing devices, processors, or computers are used, or a processing device, processor, or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, remote processing environments, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing, as only examples.

The methods illustrated in FIGS. 11-12 that perform or control the operations described herein may be performed or controlled by a processing device, processor, or a computer as described above executing instructions or software to perform one or more of the operations described herein.

Instructions or software to control a processing device, processor, or computer to implement the hardware components and perform the methods as described above may be written as computer programs, code segments, instructions or any combination thereof, for individually or collectively instructing or configuring the processing device, processor, or computer to operate as a machine or special-purpose computer to perform the operations performed by the hardware components and the methods as described above. In one example, the instructions or software include machine code that is directly executed by the processing device, processor, or computer, such as machine code produced by a compiler. In another example, the instructions or software include higher-level code that is executed by the processing device, processor, or computer using an interpreter. Based on the disclosure herein, and after an understanding of the same, programmers of ordinary skill in the art may readily write the instructions or software based on the block diagrams and the flow charts illustrated in the drawings and the corresponding descriptions in the specification, which disclose such method operations and which may be performed or implemented by any of the above described hardware components, for example.

The instructions or software to control a processing device, processor, or computer to implement the hardware components, such as discussed in any of FIGS. 1-10B, and perform or control the implementation of the methods as described above in FIGS. 11-12, and any associated data, data files, and data structures, are recorded, stored, or fixed in or on one or more non-transitory computer-readable storage media. Examples of a non-transitory computer-readable storage medium include read-only memory (ROM), random-access memory (RAM), dynamic random-access memory (D-RAM), static random-access memory (S-DRAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processing device, processor, or computer so that the processing device, processor, or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processing device, processor, or computer.

As a non-exhaustive example only, and in addition to the above explanation of potential hardware implementations of an electronic device either as the blood pressure monitor, or electronic device that includes the blood pressure monitor, or electronic device that at least includes the controller of the blood pressure monitor may also be a mobile device, such as a cellular phone, a smart phone, a wearable smart bio-signal device, a portable personal computer (PC) (such as a laptop, a notebook, a subnotebook, a netbook, or an ultra-mobile PC (UMPC), a tablet PC (tablet), a phablet, a personal digital assistant (PDA), a digital camera, a portable game console, an MP3 player, a portable/personal multimedia player (PMP), a handheld e-book, a global positioning system (GPS) navigation device, or a sensor, or a stationary device, such as a desktop PC, a television or display, a DVD player, a Blu-ray player, a set-top box, or a home appliance, an Internet of Things device, or any other mobile or stationary device, e.g., capable of wireless or network communication, for example, and capable of receiving or sensing/capturing the body data and biometric data, for example, and capable of determining a biometric state based on the received/sensed information, as well capable of informing a user of the determined biometric state, depending on embodiment.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is not limited by the detailed description, but further supported by the claims and their equivalents, and all variations within the scope of the claims and their equivalents are to be construed as being included in the disclosure.

What is claimed is:

1. A blood pressure monitor, comprising:
   a cuff configured to apply a pressure to a target portion of a body of a user;
   a pressurizer manually operated and including a rotator, the pressurizer configured to supply a fluid to the cuff, to cause the cuff to apply the pressure, through rotation of the rotator caused by an external rotational force manually applied to the blood pressure monitor to rotate the rotator;
   a depressurizer manually operated and configured to reduce the applied pressure applied by the cuff to the target portion; and
   a sensor configured to measure a pressure of the target portion.

2. The monitor of claim 1, wherein the pressurizer comprises:
   a tube connected to the cuff; and
   the rotator is configured to supply the fluid to the cuff by rotating in a state in which at least a portion of the tube is blocked.

3. The monitor of claim 2, wherein the pressurizer comprises:
   a string configured to apply the rotational force to rotate the rotator upon an external pulling of the string by the user.

4. The monitor of claim 1, wherein the pressurizer is a manually operable peristaltic pump operated by the rotation of the rotator.

5. The monitor of claim 1, wherein the pressurizer comprises:
   a ratchet configured to selectively maintain a rotation direction to be constant.

6. The monitor of claim 1, wherein the depressurizer comprises:
   a rotary damper configured to reduce the pressure applied by the cuff to the target portion at a constant rate by controlling a rotating of the rotator in a direction opposite to the rotation direction of the rotator caused by the external force, when the external force is ceased.

7. The monitor of claim 1, further comprising:
   a tube configured to supply the fluid to the cuff, and
   wherein the depressurizer comprises a valve configured to maintain a speed at which the fluid is discharged from the cuff to be constant when the external rotational force is ceased.

8. A blood pressure monitor, comprising:
   a cuff configured to apply a pressure to a target portion of a body of a user;
   a pressurizer including a rotator, the pressurizer configured to supply a fluid to the cuff, to cause the cuff to apply the pressure, through rotation of the rotator caused by a rotational force applied to the blood pressure monitor to rotate the rotator;
   a depressurizer configured to reduce the applied pressure applied by the cuff to the target portion;
   a sensor configured to measure a pressure of the target portion; and
   a tube configured to supply the fluid to the cuff,
   wherein the depressurizer comprises a valve configured to maintain a speed at which the fluid is discharged from the cuff to be constant when the external rotational force is ceased, and
   wherein the valve comprises:
   a ring configured to obstruct a flow of the fluid; and
   a support configured to support the ring based on the flow of the fluid and in which a taper, inclined in a direction in which the fluid flows, is formed.

9. The monitor of claim 1, further comprising:
   a controller configured to generate, with respect to a determined change in a blood flow of the target portion, a first feedback signal based on a determination of when pressure should be increased by application of the external force and a second feedback signal based on a determination of when the applied pressure should be decreased.

10. A blood pressure monitoring method using the blood pressure monitor of claim 1, the method comprising:
- generating a feedback signal to a user to indicate when a user should cease the manual application of the external rotational force to the blood pressure monitor;
- measuring pressure of a corresponding target portion of the user based on a determined change in blood flow; and
- outputting a calculated blood pressure of the user based on measured pressure.

11. The monitor of claim 7, wherein the valve comprises:
a ring configured to obstruct a flow of the fluid; and
a support configured to support the ring based on the flow of the fluid and in which a taper, inclined in a direction in which the fluid flows, is formed.

12. A blood pressure monitor, comprising:
a cuff configured to apply a pressure to a target portion of a body of a user;
a pressurizer manually operated and including a peristaltic pump with a rotator, the pressurizer configured to supply a fluid to the cuff, to cause the cuff to apply the pressure, through rotation of the rotator caused by a force manually applied to rotate the rotator;
a depressurizer manually operated and configured to reduce the applied pressure applied by the cuff to the target portion; and
a sensor configured to measure a pressure of the target portion.

* * * * *